United States Patent
Liu et al.

(10) Patent No.: US 9,232,924 B2
(45) Date of Patent: Jan. 12, 2016

(54) X-RAY POSE RECOVERY

(75) Inventors: Xin Liu, Eindhoven (NL); Ameet Kumar Jain, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 113 days.

(21) Appl. No.: 14/007,334

(22) PCT Filed: Mar. 29, 2012

(86) PCT No.: PCT/IB2012/051505
§ 371 (c)(1),
(2), (4) Date: Sep. 25, 2013

(87) PCT Pub. No.: WO2012/131610
PCT Pub. Date: Oct. 4, 2012

(65) Prior Publication Data
US 2014/0018670 A1     Jan. 16, 2014

Related U.S. Application Data

(60) Provisional application No. 61/470,510, filed on Apr. 1, 2011.

(51) Int. Cl.
*A61B 6/12*     (2006.01)
*A61B 6/00*     (2006.01)
*A61B 19/00*    (2006.01)

(52) U.S. Cl.
CPC .................. *A61B 6/12* (2013.01); *A61B 6/4441* (2013.01); *A61B 6/487* (2013.01); *A61B 6/547* (2013.01); *A61B 19/5244* (2013.01); *A61B 2019/5238* (2013.01); *A61B 2019/5295* (2013.01); *A61B 2019/5466* (2013.01)

(58) Field of Classification Search
CPC ........ A61B 6/12; A61B 6/4441; A61B 6/487; A61B 6/547; A61B 19/5244; A61B 2019/5238; A61B 2019/5295; A61B 2019/5466
See application file for complete search history.

(56) References Cited

U.S. PATENT DOCUMENTS 5,256,158 A * 10/1993 Tolkoff et al. ................ 604/529
6,491,429 B1   12/2002 Suhm
(Continued)

FOREIGN PATENT DOCUMENTS

DE    102009025249 A1    12/2010
WO    2005039417 A1       5/2005

OTHER PUBLICATIONS

"C-Arm Tracking and Reconstruction without an External Tracker" Jain et al, Medical Image Computing and Computer Assisted Intervention—MICCAI 2006 Lecture Notes in Computer Science Springer, Berlin, DE p. 494-502.
(Continued)

*Primary Examiner* — Long V Le
*Assistant Examiner* — Colin T Sakamoto (57) ABSTRACT

A method, system, and program product are provided for x-ray pose recovery during an endoscopic procedure. An x-ray image is taken with a C-arm at a first pose, capturing a region of an endoscope with fiducials thereon. The C-arm is moved from the first pose to a second pose at another viewing angle while maintaining the position of the endoscope. Another x-ray image is taken with the C-arm at the second C-arm pose, capturing the region of the endoscope with the fiducials thereon. The location of the fiducials on each x-ray image is determined using segmentation. An iterative optimization is performed using the locations of the fiducials in the two x-ray images to form two-dimensional projections of the three dimensional curve of the region of the endoscope with fiducials thereon to determine the three-dimensional translation and rotation of the C-arm from the first x-ray pose to the second x-ray pose.

17 Claims, 5 Drawing Sheets

(56) References Cited

U.S. PATENT DOCUMENTS

| | | |
|---|---|---|
| 2001/0036245 A1 | 11/2001 | Kienzle et al. |
| 2003/0229298 A1 | 12/2003 | Iwami et al. |
| 2004/0049095 A1 | 3/2004 | Goto |
| 2008/0097467 A1* | 4/2008 | Gruber et al. ............ 606/119 |
| 2008/0167550 A1 | 7/2008 | Weiser et al. |
| 2010/0210902 A1 | 8/2010 | Navab et al. |

OTHER PUBLICATIONS

"FTRAC—A Robust Fluoroscope Tracking Fiducial" Jain et al, Medical Physics AIP, Meville, NY vol. 32, No. 10, Sep. 29, 2005 p. 3185-3198I.

Hipwell, J.H. et al., "Intensity based 2-D registration of cerebral angiograms", Medical Imaging, IEEE Transactions on, 2003. 22(11): p. 1417-1426.

Ayad, M. et al. "C-arm pose estimation using a set of coplanar ellipses in correspondence", Proceedings of the 2010 IEEE international conference on Biomedical imaging: from nano to Macro, Rotterdam, Netherlands pp. 1401-1404, 2010,ISSN:1945-7928.

Yao J. et al. "A C-arm fluoroscopy guided progressive cut refinement strategy using a surgical robot", Computer Aided Surgery, 2000. 5(6): p. 373-390.

Fizpatrick, J.M et al. "The distribution of target registration error in rigid body point based registration". Medical Imagining, IEEE Transactions on, 2001. 20(9): p. 917-927.

* cited by examiner

X-RAY IMAGE 2

X-RAY POSE RECOVERY

This application is a national stage application under 35 U.S.C. §371 of International Application No. PCT/IB2012/051505 filed on Mar. 29, 2012, which claims priority to U.S. Application No. 61/470,510 filed on Apr. 1, 2011, the entire disclosures of which are incorporated herein by reference.

FIELD OF THE INVENTION

The invention relates to the field of x-ray guided medical intervention and more particularly to a method and system for pose recovery in an x-ray guided medical intervention.

BACKGROUND

Throughout this application, the following terms are meant to convey the accompanying definitions.

C-arm: means an intra-operative x-ray (fluoroscopy)

C-arm pose: means the three-dimensional (3D) location and orientation of the x-ray source (intensifier)

C-arm pose tracking: means to estimate the C-arm pose from one pose to another pose (the same as pose recovery). A transformation matrix encodes 3 translations and three rotations to determine a second pose from a first pose.

Bronchoscopy is a real-time modality for inspecting the internal walls of the bronchial airways and conducting subsequent diagnostic or therapeutic interventions using an endoscope. During the bronchoscopy procedure, a C-arm can be used for real-time monitoring of the location of the endoscope. However, due to the low image contrast of x-ray images, both a lesion and the airways are difficult to see. This hinders the utility of the X-ray fluoroscopy as a real-time image guidance tool in assisting bronchoscopic interventions.

One solution to the low contrast problem is to fuse a three-dimensional (3D) computed tomography (CT) image volume with two-dimensional X-ray images, and overlay a lesion to the X-ray images. The 3D image volume is fused to the 2D x-ray images by registration between the 2D images and 3D image volume. The fused visualization provides an intra-operative guidance so that one can precisely localize the lesion and identify its spatial relationship to the endoscope.

2D-3D registration between x-ray images and CT volume can image-based or fiducial-based. Image-based registration methods, which use segmentation, have comparatively small capture range and slow convergence rate. Moreover, the computational overhead for image-based registration is intensive. Also, when employing the features in the image, the result is dependent upon the accuracy of the segmentation and the characteristics of the features.

To facilitate an image-based registration method, a good initialization pose of the C-arm has to be provided to reduce searching space in the optimization scheme. However, when the C-arm moves to a different pose intra-operatively, the initialization is no longer available in the new C-arm pose. Thus, real-time fusion of 2D x-ray and 3D image volume data is not always feasible.

Fiducial-based registration addresses the problem of pose recovery after intra-operative C-arm movement. In fiducial-based registration, radiopaque devices, called fiducials are placed externally on a patient's body. The fiducials are captured in both the x-ray frame prior to intra-operative C-arm movement and the x-ray frame after intra-operative C-arm movement. Because the fiducials must be captured in both frames, they limit the size of the volume available for intra-operative guidance.

The x-ray images of the fiducials are two-dimensional in nature. If the 3D configuration of the external fiducials is unknown, for registration to happen, epipolar geometry must be used to reconstruct the 3D location of the fiducials in x-ray space. Then, the fiducials in x-ray space can be registered to fiducials in the CT space. Epipolar geometry takes the two known C-arm poses as input.

Thus, both image-based and fiducial-based 2D/3D registration require a fast and accurate C-arm pose recovery method. Unfortunately, only a very few hospitals have the expensive, high-end mobile C-arms that have the capacity to estimate or track X-ray poses. Most clinical C-arms currently used in hospitals do not provide pose tracking capability.

SUMMARY

The present invention provides a method, system and program product for x-ray pose recovery during an endoscopic procedure.

According to one embodiment a method is provided for x-ray pose recovery during an endoscopic procedure. Fiducials are attached to the surface of a distal region of an endoscope. X-ray images are taken at a first pose before a pose change and at a second pose after the pose change as two dimensional projections of a three dimensional curve of the region of the endoscope with fiducials thereon. The endoscope is held steady during the pose change. The location of the fiducials on each two-dimensional x-ray image is determined using segmentation methods. Then, an iterative optimization is performed using the two-dimensional projections of the three dimensional curve of the region of the endoscope with fiducials thereon from at least two different poses to determine the three dimensional translation and rotation of the C-arm from the first x-ray pose to the second x-ray pose.

According to one embodiment of the present invention, the iterative optimization step makes iterative estimates of the poses integrating the shape priors (such as curvature), geometric constraints that are known in advance.

According to one embodiment of the present invention, the iterative optimization step make iterative estimates of the poses utilizing the correspondence of the fiducials.

According to one embodiment of the present invention the iterative optimization further uses a prior shape model to constrain estimations in the iterative process and accelerate convergence.

According to one embodiment of the present invention, the iterative optimization further uses predetermined geometric constraints to constrain estimations in the iterative process and accelerate convergence.

According to one embodiment of the present invention the iterative optimization step comprises:

making an initial pose estimation;

reconstructing a three-dimensional shape of the region of the endoscope with fiducials thereon;

testing for convergence;

upon the test of convergence not being met, refining the three-dimensional shape of the region of the endoscope with fiducials thereon, utilizing the prior geometric constraints of the endoscope in a confined anatomic structure (e.g. endoscope has to be in the airway bronchus so the curvature of the endoscope is predefined;

making an iterative pose estimation, and repeating the steps of shape estimation and convergence testing;

upon the test of convergence being met, outputting a final pose estimation.

According to one embodiment of the present invention, at least one of shape priors and geometric constraints are compared with the three-dimensional shape reconstruction from two dimensional projections to improve convergence.

According to one embodiment of the present invention, at least one of shape priors and geometric constraints are compared with the three-dimensional shape reconstruction to test for convergence.

According to one embodiment of the present invention, a system for x-ray pose recovery during an endoscopic procedure is provided. The system comprises:

an endoscope having fiducials attached thereto;

a C-arm fluoroscope for generating fluoroscopic images of internal patient features;

a processor for processing fluoroscopic images from the C-arm and providing processed images of internal patient features for use in the procedure;

a memory operably connected to the processor and having encoded thereon:

program instructions executable by the processor to locate the fiducials using segmentation;

program instructions executable by the processor to perform an iterative optimization using the two-dimensional projections of the three dimensional curve of the fiducial-enabled region of the endoscope to determine the three dimensional translation and rotation of the C-arm from the first x-ray pose to the second x-ray pose.

According to one embodiment of the present invention, the fiducials are radiopaque rings attached to the outer surface of the endoscope.

According to one embodiment of the present invention, the iterative optimization program instructions reconstruct the three-dimensional shape of the region of the endoscope with fiducials thereon, the fiducials are spaced apart at known intervals, and the intervals are compared with the three-dimensional shape reconstruction to improve convergence.

According to one embodiment of the present invention, the iterative optimization program instructions reconstruct the three-dimensional shape of the region of the endoscope with fiducials thereon, the fiducials are spaced apart at known intervals, and the intervals are compared with the three-dimensional shape reconstruction to test for convergence.

According to one embodiment of the present invention, a computer program product is provided comprising a computer-readable, non-volatile storage medium having a program of instructions thereon, comprising:

program instructions for taking an x-ray fluoroscopic image with a C-arm at a first C-arm pose, capturing a region of an endoscope with fiducials thereon as a two dimensional projection of a three dimensional curve of the region of the endoscope with fiducials thereon;

program instructions for moving the C-arm from the first pose to a second pose at another viewing angle while maintaining the position of the endoscope;

program instructions for taking another an x-ray fluoroscopic image with the C-arm at the second C-arm pose, capturing the region of the endoscope with the fiducials thereon as another two dimensional projection of a three dimensional curve of the region of the endoscope with fiducials thereon;

program instructions for determining the location of the fiducials on each two-dimensional fluoroscopic image using segmentation; and program instructions for performing an iterative optimization using the two-dimensional projections of the three dimensional curve of the region of the endoscope with fiducials thereon to determine the three dimensional translation and rotation of the C-arm from the first x-ray pose to the second x-ray pose.

BRIEF DESCRIPTION OF THE DRAWINGS

The features and advantages of the invention will be more clearly understood from the following detailed description of the preferred embodiments when read in connection with the accompanying drawing. Included in the drawing are the following figures.

DETAILED DESCRIPTION

The present invention provides a method, system and program product for x-ray pose recovery during an endoscopic procedure. According to one embodiment of the present invention, fiducials are placed on the distal end of an endoscope before the procedure. The correspondence of internal fiducials on the endoscope and the curvature of the endoscope are utilized to perform pose recovery.

Figure 1:
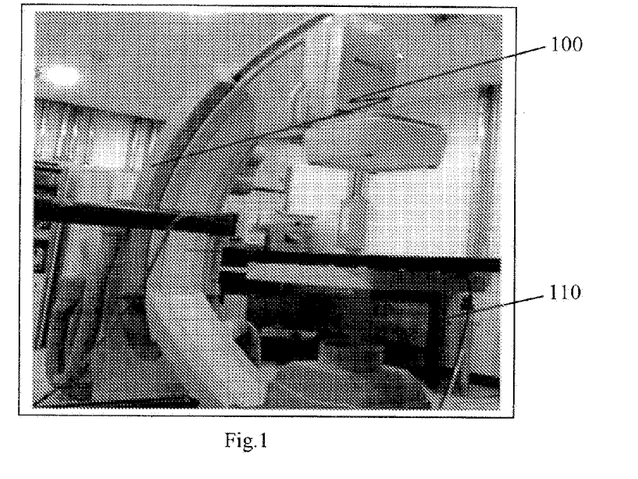
FIG. 1 is an isometric view of a C-arm used in an embodiment of the present invention.
Figure 2:
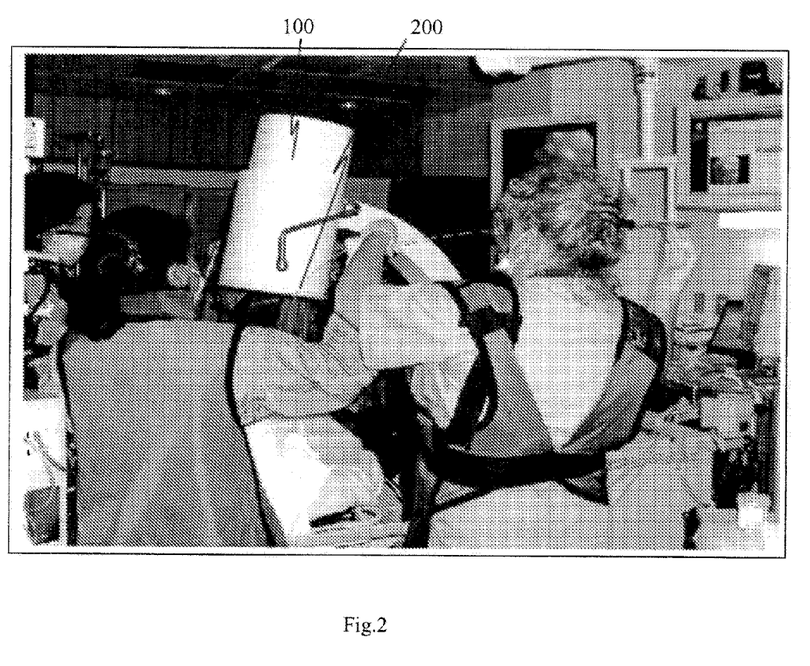
FIG. 2 shows an endoscopic procedure using a C-arm for guidance of the endoscope.

FIG. 1 shows a mobile C-arm 100 with an x-ray source 110. The mobile C-arm can be used for x-ray guided endoscopy, as shown in FIG. 2. The endoscope 200 is guided by real-time x-ray images from the c-arm 100.

Figure 3:
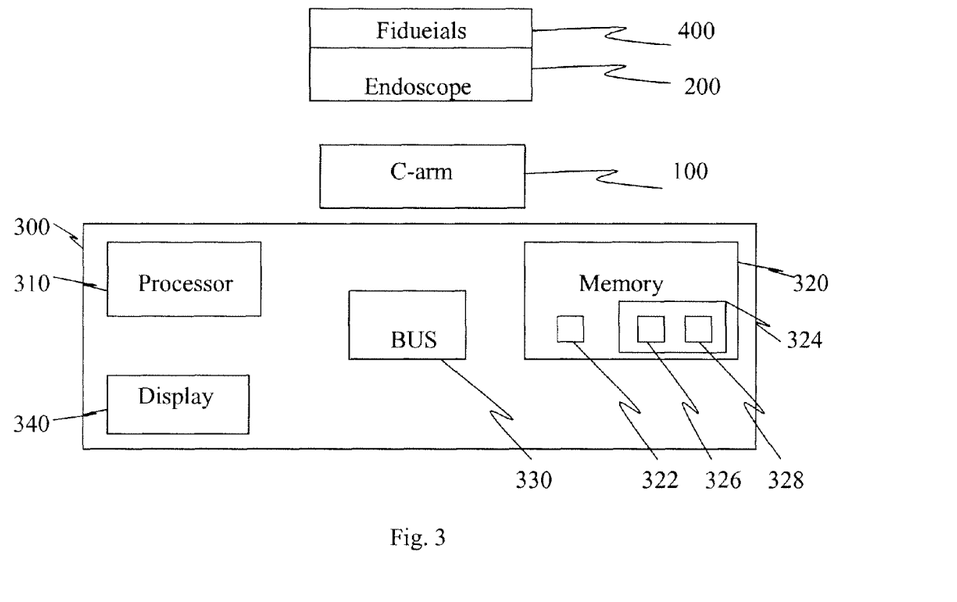
FIG. 3 is a block diagram of a system for x-ray pose recovery during an endoscopic procedure according to an embodiment of the present invention.

FIG. 3 is a block diagram of a system for x-ray pose recovery according to an embodiment of the present invention. A processing unit 300 comprises a processor 310 which is operably connected to a memory 320. According to one embodiment, they are connected through a bus 330. The processor 310 may be may be any device capable of executing program instructions, such as one or more microprocessors. The memory may be any volatile or non-volatile memory device, such as a removable disc, a hard drive, a CD, a Random Access Memory (RAM), a Read Only Memory (ROM), or the like.

A display 340 is also operably connected to the processor 310. The display may be any monitor, screen, or the like suitable for presenting a graphical user interface (GUI) capable of presenting medical images.

A C-arm 100 is operably connected to the processor 310. The C-arm provides x-ray imaging data to the processor 310 for processing to create an x-ray image of anatomical features. The x-ray image is then presented on the display 340.

The endoscope 200 is fitted with fiducials 400, which are visible in the x-ray image generated by the processor 310 and presented on the display 340. The fiducials 400 may take the form of radiopaque rings fitted to the outside surface of the endoscope 200. According to one embodiment, the fiducials 400 are disposed at the distal end of the endoscope 200, so that they will always be in the area of interest, and therefore in the viewing field of the c-arm 100. That is the area that is captured in the frame of the x-ray images. The distance between the fiducials 400 is precisely measured (or set).

Figure 4:
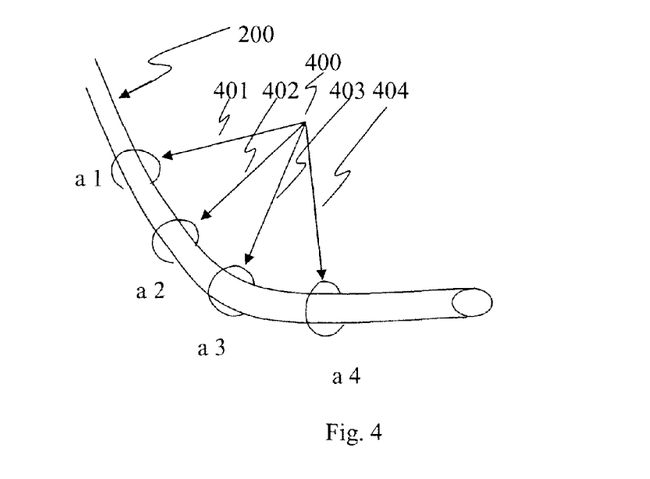
FIG. 4 shows a distal end of an endoscope with fiducials attached thereto according to an embodiment of the present invention.

FIG. 4 shows a distal end of an endoscope with fiducials attached thereto according to an embodiment of the present invention. In the illustrated embodiment, the fiducials 400 are a series of rings 401-404 attached to the outside surface of the endoscope 200 at locations $a_1$-$a_4$ respectively. Locations $a_1$-$a_4$ are known relative to the distal tip b of the endoscope 200.

According to various alternative embodiments, the fiducials may be a prescribed number of beads, spiral curves, closed curves (with partially or fully known geometries), or combinations thereof, that can be easily mounted to the endoscope. Alternatively, the fiducials may be embedded in the endoscope. The relative locations of the fiducials 400 are precisely determined, or are known a priori.

Returning to FIG. 3, the memory 320 has encoded thereon, program instructions 322 which are executable by the processor 310 to process x-ray images from the C-arm 100. In addition to the program instructions 322 for processing the image for presentation on display 340, a program of instruction 324 is also provided that performs pose recovery and registration of 2D x-ray images to a 3D image space generated prior to the procedure.

The pose recovery program of instruction 324 comprises program instructions 326 executable by the processor 310 to locate the fiducials using segmentation. That is, the fiducial location program instructions 326 locate the position of the fiducials within the 2D x-ray image frame. The fiducial location program instructions 326 may use any segmentation program suitable for locating the center of a high contrast image segment within an x-ray image. These segmentation programs are well known in the art and will not be described further in this application. The fiducial location program instructions 326 may be a part of a pose recovery program 324, or may be a separate program or module callable by the pose recovery program 324.

The pose recovery program of instructions 324 further comprises program instructions 328 executable by the processor 310 to perform an iterative optimization of a shape of the endoscope 200. According to an embodiment of the present invention, pose estimations and the two-dimensional projections of the three dimensional curve of the fiducial-enabled region of the endoscope from two different poses are used to reconstruct the three-dimensional shape of the fiducial-enabled endoscope. The, pose estimations are refined and the three-dimensional shape is reconstructed again. The process is repeated for a fixed number if iterations or until a satisfactory reconstruction is achieved. This iterative process is used to determine the poses relative to each other. That is to determine the three dimensional translation and the three-dimensional rotation of the C-arm from the first x-ray pose to the second x-ray pose. The actual position of the endoscope is held constant between the two C-arm poses, and the resulting x-ray images are used as input for the optimization process.

Figure 5:
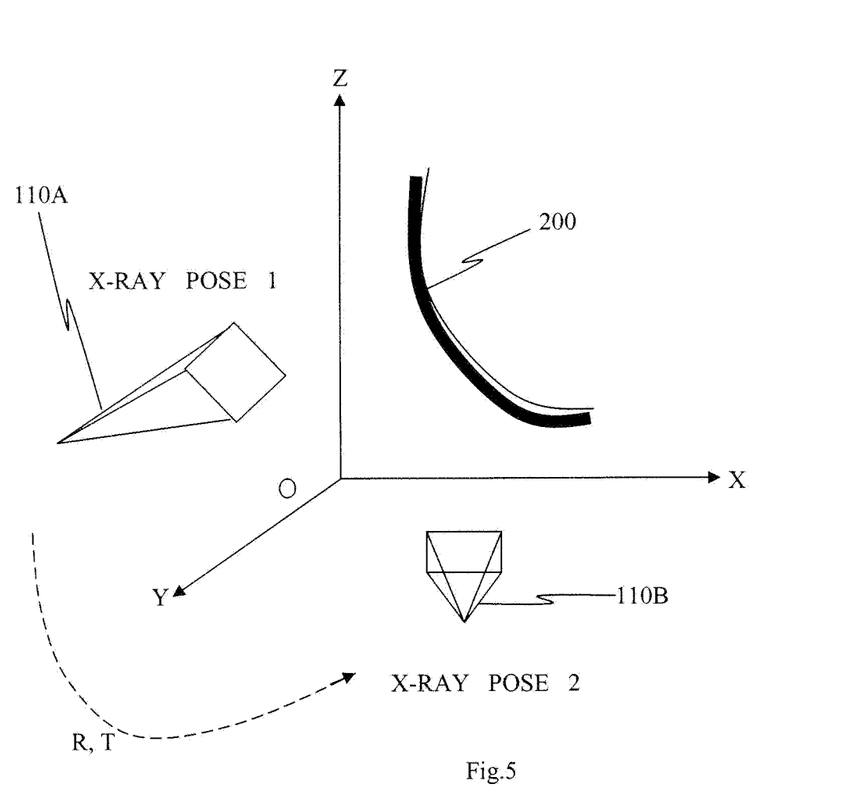
FIG. 5 shows a movement of a C-arm between x-ray poses according to an embodiment of the present invention.

FIG. 5 shows a repositioning of a c-arm according to an embodiment of the present invention. Specifically, an x-ray source 110 of the c-arm 100 is shown at a first x-ray pose 110A and at a second x-ray pose 110B relative to the endoscope 200 in 3D space. The x-ray source has six degrees of freedom: three translations (T) along the X-axis, the Y-axis, and the Z-axis, and three rotations (R) about the X-axis, the Y-axis, and the Z-axis. The endoscope 200 is held steady so that it is at the same location with the same curve for both the first pose and the second pose.

Figure 6:
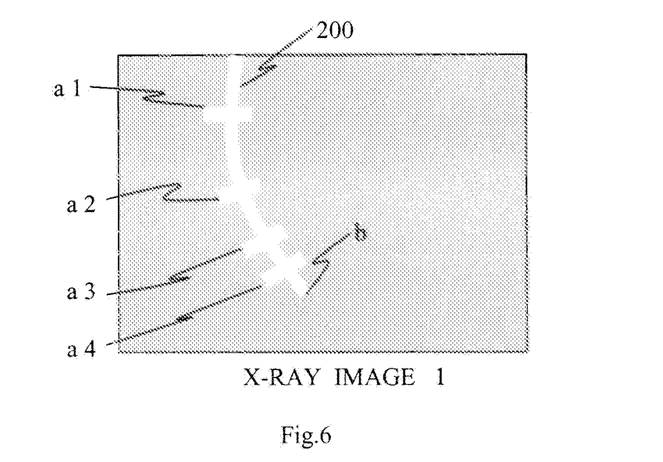
FIGS. 6 and 7 show x-ray images before and after a pose change, respectively, according to an embodiment of the present invention.
Figure 7:
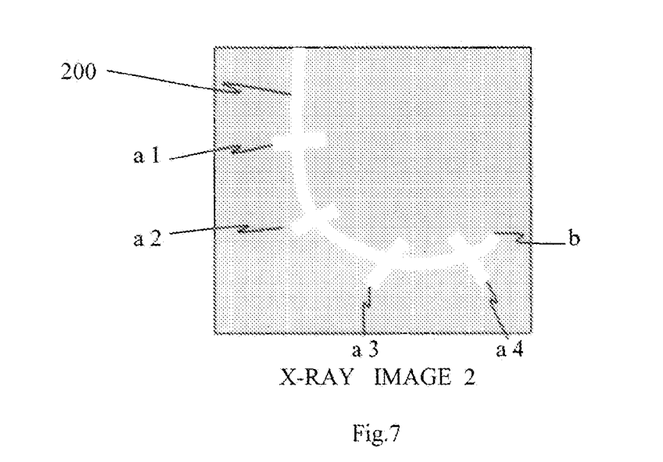

FIG. 6 is an x-ray image from the first pose in FIG. 5, and FIG. 7 is an x-ray image from the second pose in FIG. 5. The x-ray images show the two-dimensional projections of the three-dimensional curve of the endoscope from the perspective of the first pose and the second pose, respectively. Since the endoscope 200 is held steady from the first pose to the second pose, the x-ray images are projections of the same three-dimensional curve of the endoscope 200.

Provided that the 3D curve of the endoscope from the first fiducial, $a_1$ to the tip, b remains the same for the shots of the two x-ray images, the two 2D projections of this 3D curve: $S1(a_1 b)$ and $S2(a_1 b)$ may be used to perform iterative optimization of a transformation matrix from the first pose to the second pose. As previously described, according to one embodiment, a pose estimation is made, and using the pose estimation and the 2D projections of the 3D curve of the endoscope, the 3D curve is reconstructed. Then, the pose estimate is refined, and the 3D curve of the endoscope is reconstructed again. This iterative process is repeated until a termination condition is met, such as a predetermined number of iterations, a threshold change in the pose estimate or in the reconstructed 3D curve. According to one embodiment, the pose estimation comprises an estimation of the values of the transformation matrix (the three translations and three rotations of the x-ray source).

In another embodiment, the distance between each pair of fiducials is precisely determined a priori, and the correspondence of the fiducials (i.e., the fact that the fiducials are at the same point in three-dimensional space for both x-rays) may be used to perform the pose recovery estimation. That is, the distances between fiducials can be calculated using the pose estimation and the distances in the 2D projections. These calculated distances can then be compared to the pre-determined actual distances, and the pose estimation can be refined.

In yet another embodiment, the curve and the correspondence of the fiducials can be used to perform pose recovery. Based on epi-polar geometry and triangulation algorithm, if the corresponded fiducials are identified in 2D images, one should be able to recover the relative translation and rotation between two camera poses (or X-ray poses) where the 2D images were taken. If the 3D curve of the endoscope is known, the optimization will converge faster and more accurately.

According to various embodiments of the present invention, a predetermined shape of the endoscope (shape prior), predetermined geometric constraints, or a combination thereof can be added to the optimization scheme. The shape priors and geometric constraints can be used to improve the convergence speed and accuracy of the iterative optimization. According to various embodiments, the shape priors and geometric constraints may be input by a user of the system, stored in memory, or determined from stored image data, such as a pre-operative CT scan.

Shape priors can be derived from knowledge that the endoscope is positioned in a certain airway segment (e.g., in the upper right lobe vs. in the lower left lobe, the shape of the endoscope would be distinctive, conforming to the shape of the airway). The shape prior may be obtained from a medical atlas or from a patient's pre-operative CT scan.

Geometric constraints may be derived from preoperative measurements, or may be stored in memory, downloaded from a data source, or otherwise provided for a specific endoscope. Geometric constraints may include, for example, a diameter of the endoscope, thickness of the fiducials, the length of an extended biopsy needle, or any other geometric property of the endoscope or fiducials that can be obtained preoperatively.

Figure 8:
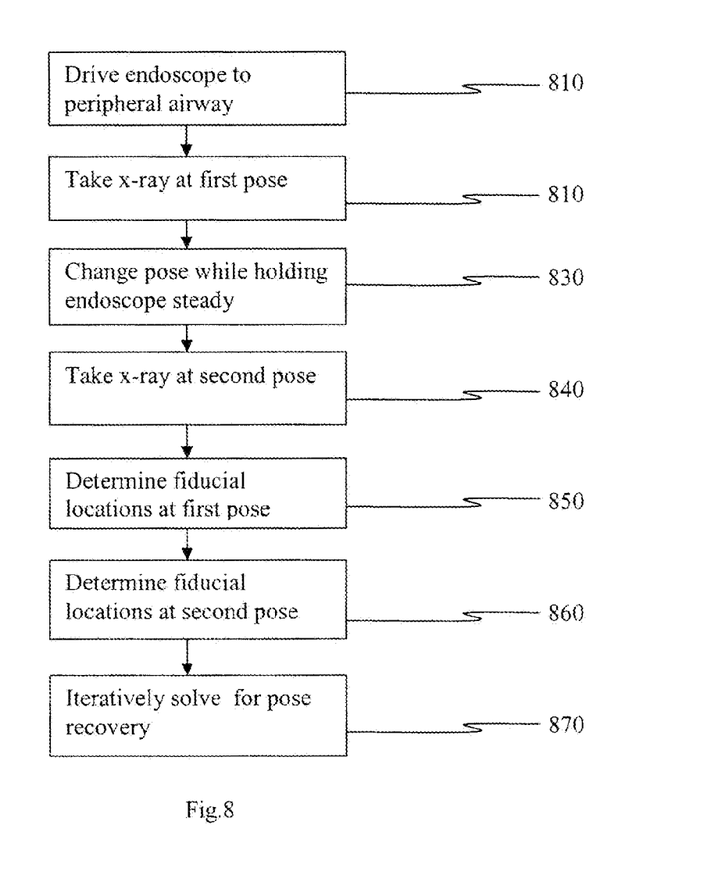
FIG. 8 is a flow diagram of a method for x-ray pose recovery during an endoscopic procedure according to an embodiment of the present invention.

FIG. 8 is a block diagram of a method for x-ray pose recovery during an endoscopic procedure according to an embodiment of the present invention. While the following description discusses a procedure in the pulmonary airways, it should be understood that this invention is not limited to this example. Rather the invention may be practiced during any endoscopic procedure.

A pulmonologist drives the endoscope 200 with the fiducial 400 attached to a peripheral airway with the C-arm at a first pose (Step 810). Because the C-arm remains in the same pose during this step, the endoscope can be tracked in real-time with fluoroscopic images.

The pulmonologist has a technician shoot an x-ray image at the first pose (Step 820). Because the fiducials 400 are attached to the distal end of the endoscope, the x-ray image, which is situated to capture the distal end of the endoscope, captures all of the fiducials.

The pulmonologist holds the endoscope 200 steady and has the technician move the C-arm, changing the pose from the first pose to a second pose (Step 830). Because the endoscope 200 is held steady, the endoscope 200 and fiducials 400 attached to it will be at the same location in three-dimensional space in x-ray images taken at the second pose at they are in x-ray images taken at the first pose.

The pulmonologist has the technician shoot an x-ray image at the second pose (step 840). The two-dimensional projection of the three-dimensional curve of the endoscope will be different in the second pose due to the change in the viewing angle caused by repositioning the C-arm.

The program instructions 326 for locating the fiducials in the pose recovery program of instruction 324 using segmentation methods are executed by the processor 310 to determine the location of the fiducials in the two-dimensional x-ray image at the first pose (Step 850). This step may optionally be performed prior to repositioning the C-arm.

The program instructions 326 for locating the fiducials in the pose recovery program of instruction 324 using segmentation methods are executed by the processor 310 to determine the location of the fiducials in the two-dimensional x-ray image at the second pose (Step 860).

The iterative optimization program instructions 328 in the pose recovery program of instruction 324 determines a transformation matrix (pose recovery) from the first pose to the second pose (Step 870).

Figure 9:
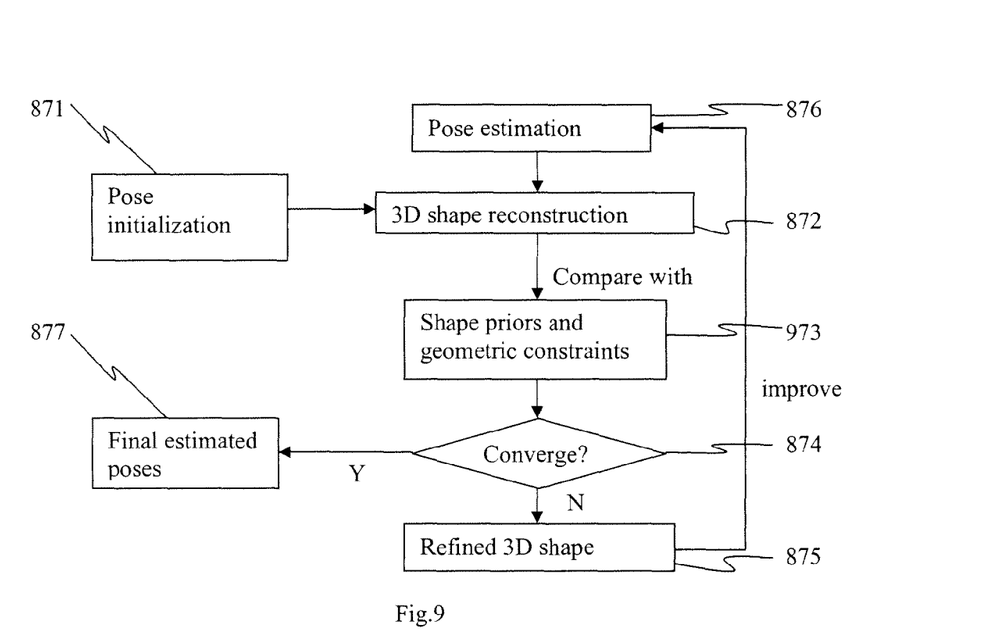
FIG. 9 is a flow diagram of iterative optimization program instructions for pose estimation according to an embodiment of the present invention.

FIG. 9 is a detailed flow diagram of the iterative optimization program instructions for pose estimation from FIG. 8, according to an embodiment of the present invention. (Step 871). The initialization is a coarse estimation of the X-ray poses based on known information such as fiducials correspondence in 2D projection images. The initial pose estimation is in the form of a transformation matrix from the location and orientation of the x-ray source 110 in the first pose to the location and orientation of the x-ray source 110 in the second pose.

Using the initial pose estimation, and the determined 2D projection locations of the fiducials for each of the first and second poses, the iterative optimization program instructions 328 in the pose recovery program of instruction 324 reconstruct the 3D shape of the endoscope 200 (Step 872).

The iterative optimization program instructions 328 receive the shape prior and geometric constraints, if provided, and compares them to the calculated 3D shape (Step 873). The shape priors and geometric constraints may be input by the technician based on preoperative measurements, or they may be retrieved from manufacturing data, or they may be acquired from preoperative CT images. The calculated shape and the shape priors or geometric constraints may be compared, for example using a goodness of fit calculation, least square residual error estimation, logistic regression, etc.

The iterative optimization program instructions 328 tests for convergence of the iterative optimization (Step 874). Convergence may be defined as a predetermined number of iterations likely to converge. In this instance, the test would comprise an iteration counter and a test to determine whether or not a threshold count has been reached.

Alternatively, convergence may be defined as a goodness of fit threshold for the 3D curve or as a threshold difference from the preceding iteration for the 3D curve, the locations of the fiducials in 3D space, or any other suitable test for convergence.

If the convergence test of step 874 is not met, then the iterative optimization program instructions 328 refine the 3D shape (step 875). That is, the estimation of the 3D curve is changed to more closely match the shape priors and/or geometric constraints. Alternatively, if there are no shape priors or geometric constraints provided, the 3D shape of the curve of the endoscope is refined by taking an iterative step to the previous shape.

The iterative optimization program instructions 328 make a new pose estimation based on the refined 3D shape of the endoscope (Step 876). That is, new estimated values for the transformation matrix are made, based on the refined 3D shape of the endoscope.

If the convergence test is met in step 874, then the iterative optimization program instructions 328 output the estimated pose as the final estimated pose (step 877).

The invention can take the form of program instructions encoded on a tangible medium. As such, the invention can be an entirely hardware embodiment, an entirely software embodiment or an embodiment containing both hardware and software elements. In an exemplary embodiment, the invention is implemented in software, which includes but is not limited to firmware, resident software, microcode, etc.

Furthermore, the invention may take the form of a non-volatile computer program product accessible from a computer-usable or computer-readable medium providing program code for use by or in connection with a computer or any instruction execution system or device. For the purposes of this description, a computer-usable or computer readable medium may be any apparatus that can contain or store the program for use by or in connection with the instruction execution system, apparatus, or device.

The foregoing method may be realized by a program product comprising a machine-readable medium having a machine-executable program of instructions, which when executed by a machine, such as a computer, performs the steps of the method. This program product may be stored on any of a variety of known machine-readable medium, including but not limited to compact discs, floppy discs, USB memory devices, and the like.

The medium can be an electronic, magnetic, optical, electromagnetic, infrared, or semiconductor system (or apparatus or device). Examples of a computer-readable medium include a semiconductor or solid state memory, magnetic tape, a removable computer diskette, a random access memory (RAM), a read-only memory (ROM), a rigid magnetic disk an optical disk. Current examples of optical disks include compact disk-read only memory (CD-ROM), compact disk-read/write (CD-R/W) and DVD.

The preceding description and accompanying drawing are intended to be illustrative and not limiting of the invention.

The scope of the invention is intended to encompass equivalent variations and configurations to the full extent of the following claims.

What is claimed is:

1. A method for x-ray pose recovery during an endoscopic procedure, comprising the steps of:
    taking an x-ray fluoroscopic image with a C-arm at a first C-arm pose, capturing a region of an endoscope with fiducials thereon as a two dimensional projection of a three dimensional curve of the region of the endoscope with fiducials thereon;
    moving the C-arm from the first C-arm pose to a second C-arm pose at another viewing angle while maintaining the position of the endoscope;
    taking another an x-ray fluoroscopic image with the C-arm at the second C-arm pose, capturing the region of the endoscope with the fiducials thereon as another two dimensional projection of a three dimensional curve of the region of the endoscope with fiducials thereon;
    determining the location of the fiducials on each two-dimensional fluoroscopic image using segmentation methods; and
    performing an iterative optimization of a shape of the endoscope using the two two-dimensional projections of the three dimensional curve of the region of the endoscope with fiducials thereon to determine the three dimensional translation and rotation of the C-arm from the first C-arm pose to the second C-arm pose.

2. The method of claim 1, wherein the translation and rotation are provided as a transformation matrix.

3. The method of claim 1, wherein the iterative optimization step optimizes a curve of the endoscope at the fiducials.

4. The method of claim 1, wherein the optimization step optimizes correspondence of locations of the fiducials.

5. The method of claim 1, wherein the iterative optimization further uses a prior shape model to constrain estimations in the iterative process and accelerate convergence.

6. The method of claim 1, wherein the iterative optimization further uses predetermined geometric constraints to constrain estimations in the iterative process and accelerate convergence.

7. The method of claim 1, wherein the iterative optimization step comprises:
    making an initial pose estimation;
    reconstructing a three-dimensional shape of the region of the endoscope with fiducials thereon;
    testing for convergence;
    upon the test of convergence not being met, refining the three-dimensional shape of the region of the endoscope with fiducials thereon;
    making an iterative pose estimation, and repeating the steps of shape estimation and convergence testing;
    upon the test of convergence being met, outputting a final pose estimation.

8. The method of claim 7, wherein at least one of shape priors and geometric constraints are compared with the three-dimensional shape reconstruction to improve convergence.

9. The method of claim 7, wherein at least one of shape priors and geometric constraints are compared with the three-dimensional shape reconstruction to test for convergence.

10. The method of claim 1 wherein the fiducials comprise radiopaque rings attached to the outside surface of the endoscope.

11. A system for x-ray pose recovery during an endoscopic procedure, comprising:
    an endoscope having fiducials attached thereto;
    a C-arm fluoroscope for generating fluoroscopic images of internal patient features;
    a processor for processing fluoroscopic images from the C-arm and providing processed images of internal patient features for use in the procedure;
    a memory operably connected to the processor and having encoded thereon:
    program instructions executable by the processor to locate the fiducials using segmentation;
    program instructions executable by the processor to perform an iterative optimization of a shape of the endoscope using two two-dimensional projections of a three dimensional curve of a fiducial-enabled region of the endoscope to determine a three dimensional translation and rotation of the C-arm from a first C-arm pose to a second C-arm pose.

12. The system of claim 11, wherein the fiducials are radiopaque rings attached to the outer surface of the endoscope.

13. The system of claim 11, wherein the iterative optimization program instructions optimize the curve of the endoscope at the fiducials.

14. The system of claim 11, wherein the optimization program instructions optimize the correspondence of the fiducials.

15. The system of claim 11, wherein the iterative optimization program instructions reconstruct the three-dimensional shape of the region of the endoscope with fiducials thereon, the fiducials are spaced apart at known intervals, and the intervals are compared with the three-dimensional shape reconstruction to improve convergence.

16. The system of claim 11, wherein the iterative optimization program instructions reconstruct the three-dimensional shape of the region of the endoscope with fiducials thereon, the fiducials are spaced apart at known intervals, and the intervals are compared with the three-dimensional shape reconstruction to test for convergence.

17. A computer program product comprising a computer-readable, non-volatile storage medium having a program of instructions thereon, comprising:
    program instructions for taking an x-ray fluoroscopic image with a C-arm at a first C-arm pose, capturing a region of an endoscope with fiducials thereon as a two dimensional projection of a three dimensional curve of the region of the endoscope with fiducials thereon;
    program instructions for moving the C-arm from the first C-arm pose to a second C-arm pose at another viewing angle while maintaining the position of the endoscope;
    program instructions for taking another an x-ray fluoroscopic image with the C-arm at the second C-arm pose, capturing the region of the endoscope with the fiducials thereon as another two dimensional projection of a three dimensional curve of the region of the endoscope with fiducials thereon;
    program instructions for determining the location of the fiducials on each two-dimensional fluoroscopic image using segmentation; and
    program instructions for performing an iterative optimization of a shape of the endoscope using the two two-dimensional projections of the three dimensional curve of the region of the endoscope with fiducials thereon to determine the three dimensional translation and rotation of the C-arm from the first C-arm pose to the second C-arm pose.

* * * * *